United States Patent [19]

Sikkenga

[11] Patent Number: 4,550,091

[45] Date of Patent: Oct. 29, 1985

[54] NON-AQUEOUS EXCHANGE OF ACIDIC SITES ON MOLECULAR SIEVES

[75] Inventor: David L. Sikkenga, Wheaton, Ill.

[73] Assignee: Standard Oil Company (Indiana), Chicago, Ill.

[21] Appl. No.: 624,047

[22] Filed: Jun. 25, 1984

[51] Int. Cl.$^4$ .......................... B01J 37/30; B01J 31/32
[52] U.S. Cl. ........................................ 502/62; 502/85; 502/202
[58] Field of Search ...................... 502/60, 62, 64, 85, 502/202

[56] References Cited

U.S. PATENT DOCUMENTS 4,414,005 11/1983 De Bievre et al. ............... 502/62 X
4,472,517 9/1984 Tsao et al. ............................ 502/62
4,477,583 10/1984 Rodewald ........................ 502/62 X Primary Examiner—Carl F. Dees
Attorney, Agent, or Firm—William C. Clarke; William T. McClain; William H. Magidson

[57] ABSTRACT

Surface-active catalytic sites are deactivated on catalyst support materials wherein the catalyst comprises crystalline aluminosilicate or borosilicate molecular sieve catalytic compositions without deactivating all acidic sites of the molecular sieve. Resulting catalyst compositions are useful in dehydrogenating and/or isomerizing hydrocarbons.

9 Claims, No Drawings

NON-AQUEOUS EXCHANGE OF ACIDIC SITES ON MOLECULAR SIEVES

FIELD OF THE INVENTION

The field of this invention relates to a process for selective exchange of undesirable acidic sites on a catalyst containing both a support and molecular sieve and to catalytic compositions resulting therefrom wherein cracking activity of the catalyst in dehydrogenation and isomerization reactions is reduced and conversion or selectivity is increased. The process is selective in that while exchanging acid sites causing cracking activity, the process does not extensively neutralize the acidic sites which catalyze dehydrogenation and isomerization reactions. The selective exchange of undesirable acidic sites can be used to neutralize these undesirable acidic sites so that the resultant catalyst contains active sites primarily for the desired reaction. Selective exchange of acidic sites can be used to place an active component on the catalyst to yield a bifunctional catalyst. Neutralizing the undesirable acidic sites has resulted in improved selectivity in dehydroisomerization of n-butane to isobutylene and isomerization of n-butene to isobutene.

BACKGROUND OF THE INVENTION

A large number of catalyst materials exhibit acidic sites on the surface and within the pores of the catalyst. Specific catalyst support materials displaying this property include synthetic aluminosilicates, natural aluminosilicates, silica gels, and alumina. Preferred catalysts useful in the invented process are crystalline aluminosilicate or borosilicate zeolites termed molecular sieves.

Molecular sieves are known to have uniformly structured pores in which ion exchange sites exist. These sites are readily made into the acid form by known techniques and thus provide a highly active acidic site within the geometric constraints of the sieve pore. This combination of acidity and geometrical constraint yields a catalytic site which tends to be very active for certain acid catalyzed reactions but inactive for other reactions which are more sterically demanding.

Since the molecular sieve is originally made in the form of a fine powder, some method of supporting it is required as larger particles must be utilized to allow its use in commercial reactors. However, many supports, while binding the sieve into usefully sized particles, also contain intrinsic acid sites of their own. These support acid sites can give rise to undesirable acid-catalyzed reactions which would not be catalyzed by the sieve acid sites. A common method of neutralizing acidic sites on a catalyst is by exchange with an alkali metal such as sodium or potassium. However, any aqueous alkali metal solution would exchange both the support and the sieve sites rendering the catalyst inert for acid catalyzed reactions.

A process has been found for selective exchange of undesirable acidic sites on the surface of a catalyst containing both a support and a molecular sieve. This process is selective in that while exchanging the support acid sites causing cracking activity, it does not extensively neutralize the acidic sites which catalyze dehydrogenation and isomerization reactions. The selective exchange of undesirable acidic sites apparently can be used to neutralize these acidic sites so that the resultant catalyst will contain only desirable active sites. Selective exchange of undesirable acidic sites can also be used to place an active component only on the catalyst support to yield a bifunctional catalyst.

Modification of the activity of catalysts employing certain crystalline aluminosilicate zeolite compounds to improve selectivity of the resulting catalytic reaction is known in the art. However, these modifications have been directed to modification of the crystalline aluminosilicate and borosilicate compounds and not to support material, if such is part of the catalyst composition. For example, U.S. Pat. No. 3,251,897 teaches use of an aluminosilicate catalyst that has been metal base exchanged or hydrogen acid exchanged, or both, so as to have a minimum level of catalytic activity, thus producing a high level of alkylation products particularly at low temperatures both in liquid and mixed phases. This minimum level of activity is taught as depending upon the degree of exchange of the metal from the sites within the aluminosilicate catalyst either with the base exchanged metal, or in the case of acid exchanged, with hydrogen or both. U.S. Pat. No. 2,904,607 teaches the reaction of alkyl aromatic compounds by reacting aromatic and olefinic hydrocarbons using a crystalline non-acidic aluminosilicate catalyst having pore openings adequate to admit freely the individual aromatic and olefinic molecule. The pore openings are from 6 to 15 Å, i.e., too large an opening not permitting high activity because of concomitant decrease in surface area. Pore size openings can be modified by base-exchanging the prepared sodium zeolite catalyst with another ion, such as calcium, to form a calcium sodium aluminosilicate. U.S. Pat. No. 3,682,996 describes crystalline aluminosilicate zeolites modified by reaction with an organic substituted silane. The preferred zeolite species has a pore size greater than 7 Å in diameter, since such pore size will readily accommodate the organosilane into the porous structure of the aluminosilicate. The modified catalytically active zeolite catalyst can be employed in certain shape selective catalyzed reactions since, due to the substantial decrease in sorption properties, only molecules of special size will pass through the zeolite and undergo catalytic change. U.S. Pat. No. 3,698,157 describes an improved method for separation and isolation of individual components in a $C_8$ aromatic mixture by contacting the mixture with an aluminosilicate zeolite which has been modified by contact with an organic-radical substituted silane. U.S. Pat. No. 4,100,215 describes preparation of a zeolite catalyst which has been contacted with a surface modifying agent capable of deactivating catalytic sites located on the external surface of the zeolite. Treatment involves contact with a suitable compound of silicon or nitrogen of a size sufficiently large to be unable to penetrate the zeolite pore structure. Representative of these compounds are phenyl carbazole, dimethyl dichloro silane, trimethyl chlorosilane, substituted phenyl acidines, and organic substituted silanes. The resulting catalyst is useful in a process for the selective production of paraxylene by methylation of toluene.

While the above-mentioned prior art is considered of interest in connection with the subject matter of the present invention, the selective process described herein for selective exchange of acidic sites on the surface of the support of the zeolite sieve component has not, insofar as is known, been heretofore disclosed. The resultant catalyst selectively isomerizes hydrocarbons with reduced by-product formation. Selective exchange of support acidic sites can be used to place an active component primarily on the catalyst support to yield a bifunctional catalyst.

It is an object of the present invention to provide an improved catalyst composition comprising a crystalline aluminosilicate or borosilicate molecular sieve and a support material wherein acid sites on the surface of the support are exchanged with an organo metal compound while the acid sites of the zeolite are not completely exchanged.

It is an object of this invention to provide an improved catalyst composition comprising a crystalline aluminosilicate or borosilicate molecular sieve and a support material wherein the acid sites on the surface of the support material are exchanged with an active component while the acid sites of the zeolite are not completely exchanged, thus providing a bifunctional catalyst.

It is an object of this invention to provide a process for selective exchange of acidic sites on the surface of the support material in a catalyst containing both support material and a crystalline aluminosilicate or borosilicate molecular sieve while the acid sites of the zeolite are not completely exchanged.

Other objects will appear hereinafter.

SUMMARY OF THE INVENTION

Surface-active catalytic sites are deactivated on catalyst support materials wherein the catalyst composition comprises crystalline aluminosilicate or borosilicate molecular sieve catalytic compositions without deactivating all acid sites of the molecular sieve. The resulting catalyst compositions are useful in dehydrogenating and/or isomerizing hydrocarbons. Active components can be placed on the surface-active catalytic sites of the support materials to yield bifunctional catalysts.

DETAILS OF THE INVENTION

This invention relates to a process for selective exchange of acidic sites on the surface of the support material in a catalyst composition containing both a support material and a crystalline aluminosilicate or borosilicate molecular sieve, and the catalytic compositions resulting therefrom wherein cracking activity of the catalyst in dehydrogenation and isomerization reactions is reduced and conversion or selectivity is increased.

In order to perform the selective exchange process of this invention, four components are needed:

1. The catalyst—preferably in the form in which it will be packed into a reactor.
2. A metal cation which will exchange with the acidic site of the catalyst and will bind to an organic ligand. Sodium and potassium are examples. In addition, it is often useful if the ligand is one which is readily removable from the catalyst during calcination.
3. An organic ligand which will allow the metal cation to dissolve in an organic solvent. Such ligands must be too large to enter the pores of the sieve. These ligands include certain organic anions such as commercially available dioctyl sulfosuccinate and crown ethers. Dioctyl sulfosuccinate (I) is $RCH_2CH(R)SO_3^-$ wherein R is $CH_3(CH_2)_3CH(C_2H_5)CH_2OOC-$. Crown ethers are a class of organic substances which are soluble in common organic solvents and possess the ability to solvate metal cations. Commercially available examples of crown ethers are 15-Crown-5 (II), 18-Crown-6 (III), and dicyclohexano-18-Crown-6 (IV).

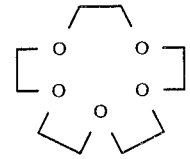

II

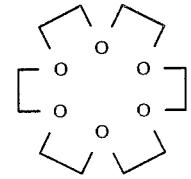

III

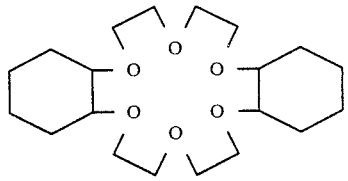

IV

Different crown ethers are specific for different metal cations. The proper choice of crown ether to solvate particular metal cations has been reviewed (D. E. Fenton in *Bioenergetics and Thermodynamics: Model Systems*, 1980, p. 275–296 and J. J. Christensen et al., *Chemical Reviews*, 74, (3) 1974, p. 351–384) and is known to those skilled in the art.

4. A non-aqueous solvent. The solvent must dissolve the organic ligand but not the isolated metal cation. The solvent provides the mobility to allow the metal cation-organic complex to reach the support site.

The apparatus used for the exchange must be constructed to allow the dissolved metal complex to reach the catalyst. A simple container will satisfy this requirement. A preferred method when using the crown ether-ligand is to recycle the solvent/crown ether mixture over both a metal salt and the catalyst in separate chambers. One such arrangement can use a pump to recycle the solvent/crown ether mixture over the metal salt first, then over the catalyst. The following reactions take place in this system:

At the metal salt surface:

Crown ether$_{(solution)}$ + M$^+$X$^-$$_{(solid)}$ → Crown ether . . . M$^+$ . . . X$^-$$_{(solution)}$ At the support acid site:

Support - - - OH + Crown ether . . . M$^+$ . . . X$^-$$_{(solution)}$ → Support . . . OM + Crown ether + HX While the crown ether can transport the cation to the unhindered support acid sites, because of its size it cannot fit into the molecular sieve pores and thus cannot transport the cation to the acid sites within the sieve pores. Thus the metal cation may be transported only to sites accessible to the crown ether. Furthermore, it should be noted that the crown ether need only be present in small quantities since after transporting one cation to the exchange site it is able to pick-up another metal cation and repeat the cycle.

When using an anionic ligand such as dioctyl sulfosuccinate (I), the metal complex of the ligand can be used directly to contact the catalyst.

A large number of catalyst support materials exhibit activity due to the presence of acidic sites. Specific catalyst support materials that exhibit this activity include alumina, silica gels, borosilicates, synthetic, aluminosilicates, and natural aluminosilicates termed molecular sieves.

Suitable non-aqueous solvents include aromatic compounds including benzene, toluene, and o-, m-, p-xylenes, and aliphatic hydrocarbons of from 6 to 12 carbon atoms. Suitable aliphatic hydrocarbons include n-hexane, heptane, octane, etc., to dodecane. It is required that the non-aqueous solvent be able to dissolve the metal-ligand complex without dissolving the metal cation alone.

Embodiments of the process of the present invention can be found in the following examples. These embodiments and examples are presented for purposes of illustration only and are not intended to limit the scope of the invention.

EXAMPLE I

In the single-step dehydroisomerization of butane to isobutylene a bifunctional catalyst is required to both dehydrogenate butane to n-butenes and isomerize butenes to isobutylene. One such catalyst (U.S. Pat. No. 4,433,190) is comprised of Amoco Molecular Sieve (HAMS-1B) and platinum on an alumina support. The desired isomerization reactions occur with minimal by-product formation at the acidic site in the sieve pores. However, the acidic sites (Al-OH) on the surface of the support cause olefin dimerization followed by cracking. Thus the process described in this invention has been utilized successfully to neutralize many of these harmful support acidic sites as follows:

A mixture of 2.2 g KOH pellets and 400 ml benzene was boiled to azeotropically remove any water from the mixture. The mixture was then cooled under nitrogen and used to flush a glass column prior to packing the glass column with catalyst.

Into the reservoir were placed 1.2 g of dicyclohexano-18-crown-6 (III) and 25 ml of the dried benzene. The glass column was packed with 5.0 g catalyst and 0.3 g of the dried KOH pellets. The pump was started and the benzene/crown ether solution was allowed to recycle for about 8 hours at a rate of about 3 ml/min.

The column was then flushed with 100 ml pure benzene and the catalyst was dried using a nitrogen purge. After removal from the column, the catalyst was dried and calcined in air prior to analysis. Table I indicates the results of analysis by Inductively Coupled Plasma (ICP) and Digisorb-Adsorption before and after treatment. Analytical results are in percent by weight and parts per million (ppm).

TABLE I

Comparison of Untreated and K+ Treated Catalysts for Butane Dehydroisomerization*

| Run No. | Untreated 6476-40-33 | K+ Treated 6476-46-37 |
|---|---|---|
| Hrs on Stream (Since Regen) | 67.5 | 67.5 |
| % n-Butane Conversion | 45.3 | 44.2 |
| % Non-C4 By-Products | 9.51 | 5.55 |
| % Selectivity to Butylenes | 72.5 | 80.7 |
| % Selectivity to Isobutane | 6.52 | 6.74 |

TABLE I-continued

Comparison of Untreated and K+ Treated Catalysts for Butane Dehydroisomerization*

| Run No. | Untreated 6476-40-33 | K+ Treated 6476-46-37 |
|---|---|---|
| Isobutylene as % of Butylenes | 35.7 | 32.3 |
| % Isobutylene in Reactor Effluent | 11.7 | 11.5 |
| Analyses* | | |
| Al (wt) % | 13.5 | 13.6 |
| Pt (wt) % | 0.77 | 0.77 |
| Na, ppm | 68 | 133 |
| K ppm | 68 | 830 |
| Surface Area | 407 m²/g | 403 m²/g |
| Pore Area | 0.85 cc/g | 0.8 cc/g |

*Both samples were taken under identical conditions.

Samples of both untreated and treated catalyst were then evaluated under identical conditions for the conversion of butane to butenes and isobutylene. Table I is representative of the analytical differences between the two catalysts and demonstrates clearly that, although by-product formation is reduced with the K+ treated catalyst, desirable activity is retained. The data in Table I were obtained after both catalysts had been regenerated once and indicate that the K+ treated catalyst is stable to regeneration.

EXAMPLE II

A 40% (platinum exchanged borosilicate molecular sieve) on Al$_2$O$_3$ (Run No. 6228-174-0) was prepared in the following procedure.

314.3 g Al$_2$O$_3$ sol (containing 9.8% Al$_2$O$_3$) and 20.0 g Pt exchanged borosilicate molecular sieve (1.24% Pt) were added to a blender. After blending at high speed for four minutes the mixture was transferred into a glass dish. To the mixture there was added 15 ml of 29% NH$_4$OH in H$_2$O. The NH$_4$OH caused gelling and further mixing was performed for 15 minutes until uniform.

The gel was then dried for four hours at 150° C. and calcined at 300° C. for four hours. The calcined solid was crushed and sieved to yield the desired catalyst particles (0.0164–"0.0278", 24–40 U.S. mesh).

Analyses performed on this catalyst II are shown in Table II. This catalyst was not evaluated but was used to prepare catalysts in Examples III–V.

EXAMPLE III

The following example illustrates selective neutralization of catalyst sites which can yield by-products.

Dioctyl sodium sulfosuccinate (DSS) is a commercially available chemical which contains a sodium cation bonded to a large organic anion. DSS is also soluble in hydrocarbons making it ideally suited to selectively neutralize exterior acidic sites of a molecular sieve.

The neutralization was performed as follows:

A solution of 10 ml toluene and 0.20 g DSS was added uniformly to a 5.0 g sample of the catalyst prepared in Example II. After allowing the toluene to evaporate, the catalyst was calcined at 300° C. for four hours.

A sample (1.9 g) of this catalyst was packed into a 1 cm (ID) reactor and purged with hydrogen at 525° C. for 1–2 hours. A mixture of butane and hydrogen was passed over the catalyst and 25 ml H$_2$S was added to reduce cracking. After the catalyst had been on-stream for 24 hours, a sample of the reactor effluent was analyzed. The hydrocarbon analysis is reported in Table III along with the reaction conditions. Both n-butenes and isobutylene were formed with a combined selectivity of 74.1% based on the butane converted.

EXAMPLE IV

A second sample of catalyst II was treated with DSS as in Example III except that the amount of DSS per gram catalyst was increased to 0.15 g. The higher sodium loading on catalyst IV is confirmed by the analyses (Table II) indicating 7200 ppm sodium on the calcined catalyst.

Catalyst IV was evaluated under conditions identical to Example III and the catalyst performance results are shown in Table III. In this case selectivity to butylenes was 72.7% of the butane converted.

EXAMPLE V

To illustrate how the DSS treatment improves catalyst performance, Example V is included as a control. To try to simulate the catalyst treatment of Examples III and IV but without depositing sodium on the catalyst, the following experiment was performed:

A benzene solution of dicyclohexano-18-crown-6 (3.4 g benzene and 0.006 g crown ether per gram catalyst) was mixed with catalyst II and the benzene was evaporated. The catalyst was then calcined exactly as in Examples III and IV. This step utilized the large, bulky crown ether to simulate the effect of the hydrocarbon portion of DSS. The analyses in Table II indicate that the catalyst did not contain detectable amounts of sodium or potassium, being less than 30 ppm.

The performance of this control catalyst is shown in Table III. Although the butane conversion is essentially the same as in Examples III and IV the selectivity to butylenes is 5-7 percent poorer.

TABLE II

| Analytical Data for Catalysts in Examples II–V | | | | |
|---|---|---|---|---|
| Catalyst Prep - Example | II | III | IV | V |
| Run No. | 6228-174-0 | 7278-51 | 7278-58 | 7278-19-3 |
| g DSS/ g Catalyst | 0 | 0.04 | 0.15 | 0 |
| Analyses | | | | |
| Na (ppm) | 71 | 1900 | 7200 | <30 |
| K (ppm) | 86 | <50 | <50 | <30 |
| Pt (%) | 0.39 | 0.47 | 0.51 | |
| Al (%) | 29.8 | 29.7 | 26.6 | |
| Si (%) | 16.6 | 16.3 | 16.2 | |
| B (%) | 0.12 | 0.14 | 0.16 | |
| BET Surface Area (m²/g) | 506 | 493 | 470 | |
| Pore Volume (cc/g) | 0.933 | 0.971 | 0.919 | |
| Avg. Pore Radius (Å) | 47 | 49 | 48 | |
| Catalyst Evaluation Run No. | — | 7294-166 | 7876-1 | 7860-30 |

TABLE III

Performance of DSS-Treated Catalysts for Butane Dehydroisomerization

| Catalyst | | | |
|---|---|---|---|
| Run Number | 7294-166-9 | 7876-1-9 | 7876-30-9 |
| Example Number | III | IV | V |
| Na (ppm) | 1900 | 7200 | <30 |
| Performance | | | |
| Conditions for all samples: | n-Butane feed WHSV = 2.5 H$_2$/Butane mole ratio = 2.0 540° C., 0.5 atm | | |
| % n-Butane Conversion | 39.9 | 41.9 | 42.0 |

TABLE III-continued

Performance of DSS-Treated Catalysts for Butane Dehydroisomerization

| Selectivities | | | |
|---|---|---|---|
| To Butylenes | 74.1 | 72.7 | 67.1 |
| To Isobutane | 4.9 | 3.6 | 4.9 |
| To Other By-Products | 21.0 | 23.6 | 28.0 |
| % Isobutylene in C$_4$ Olefins | 36.6 | 33.7 | 38.0 |

EXAMPLE VI

The following example illustrates improvement of an isomerization catalyst via neutralization of acid sites.

A catalyst containing 20% crystalline borosilicate molecular sieve and 80% Al$_2$O$_3$ support was made using a procedure similar to Example III except that the sieve contained no active metal. To a 5.0 g sample of the catalyst was added 20 ml of a toluene solution containing 0.19 g DSS. After mixing the catalyst with the toluene solution the toluene was evaporated and the catalyst calcined at 300° C. for four hours in air. A control catalyst received the identical treatment except that the toluene solution contained no DSS.

The analyses of both catalysts are reported in Table IV and illustrate that the sodium content is the only significant change in catalyst composition. The catalyst structure appears to be identical for the control and the DSS-treated catalyst.

Both samples were evaluated in a fixed bed reactor (as in Example III) using a mixture of 1-butene and hydrogen as the feed. Table V documents the results. Under the evaluation conditions, as ideal catalyst would have isomerized the 1-butene to the thermodynamic equilibrium of just the C$_4$ olefins with the product composition shown in Table V. The control catalyst, however, yielded significant amounts of lower and higher carbon number hydrocarbons with a selectivity to 2-butenes plus isobutylene of only 54% at 88.7% conversion. Significant cracking of the 1-butene feed was observed. The DSS treated catalyst, however demonstrated a selectivity of almost 85% with a conversion of 79.8%, and less cracking. Thus the DSS treatment reduced conversion by only 8.9% while improving selectivity to the desired C$_4$ olefins by 30.9% with reduced cracking.

TABLE IV

| Catalyst Analyses for Example VI | | |
|---|---|---|
| Catalyst Run Number | Control 7278-102-B | DSS Treated 7278-102-A |
| Composition | | |
| K | <50 ppm | <70 ppm |
| Na | 124 ppm | 1760 ppm |
| B | 0.09% | 0.12% |
| Si | 9.64% | 9.29% |
| C | 0.15 | 0.17 |
| H | 1.10 | 1.19 |
| Structure | | |
| Surface Area (m²/g) | 329 | 328 |
| Pore Volume (cc/g) | 0.625 | 0.626 |
| Avg. Pore Radius (Å) | 36 | 36 |

TABLE V

Effect of DSS Treatment on an Isomerization Catalyst of Example VI

| Conditions for both samples: | 525° C., 7.5 psia WHSV = 7.6 g feed/g cat/hr H$_2$/1-Butene = 2.0 mole ratio |
|---|---|

TABLE V-continued
Effect of DSS Treatment on an Isomerization Catalyst of Example VI

| Catalyst 20% HAMS-1B/Al$_2$O$_3$ | Control | At C$_4$ Olefin Equilibrium | With DSS Treatment |
|---|---|---|---|
| Product Analysis (Wt %) | | | |
| Run No. | | 7871-126-4 | 7871-123-4 |
| Component | | | |
| C$_1$–C$_3$ | 24.6 | — | 5.09 |
| Butanes | 3.64 | — | 1.29 |
| 1-Butene | 11.2 | 14.1 | 20.0 |
| 2-Butenes | 24.3 | 40.9 | 43.5 |
| Isobutylene | 23.6 | 44.5 | 24.2 |
| C$_5$+ | 12.7 | — | 5.90 |
| Conversions and Selectivities | | | |
| 1-Butene Conversion | 88.7 | 85.9 | 79.8 |
| Selectivity to 2-Butene Plus Isobutene | 54.0 | | 84.9 |
| Selectivity to C$_1$–C$_3$ By-Products | 27.7 | | 6.4 |
| Selectivity to Butanes | 4.0 | | 1.6 |
| Selectivity to C$_5$+ By-Products | 14.3 | | 7.4 |

What is claimed is:

1. A process for non-aqueous exchange of acidic sites on catalysts comprising a support material having acidic sites and a molecular sieve wherein cracking activity of said catalyst is reduced and conversion and/or selectivity is increased in dehydroisomerization and isomerization reactions which process comprises contacting said catalyst with a metal cation-organic ligand complex dissolved in a non-aqueous solvent wherein said organic ligand solvates said metal cation whereby said metal cation exchanges with and deactivates acidic sites of the catalyst support material without deactivating all acidic sites of said molecular sieve at a temperature of 0°–150° C. and a pressure of 1–50 atmospheres.

2. The process of claim 1 wherein said support material is selected from the group consisting of alumina, silica gel, synthetic alumina-silicates and natural aluminosilicates and borosilicates.

3. The process of claim 1 wherein said molecular sieve is a crystalline aluminosilicate.

4. The process of claim 1 wherein said molecular sieve is a borosilicate.

5. The process of claim 1 wherein said metal cation is a Group IA metal cation.

6. The process of claim 5 wherein said metal cation is selected from the group consisting of sodium and potassium.

7. The process of claim 1 wherein said organic ligand is selected from the group consisting of dioctyl sulfosuccinate and a crown ether.

8. The process of claim 7 wherein said crown ether is selected from the group consisting of 15-Crown-5, 18-Crown-6 and dicyclohexane-18-Crown-6.

9. The process of claim 1 wherein said solvent is selected from the group consisting of benzene, o, m, p-xylene, toluene and aliphatic hydrocarbons of from 6 to 12 carbon atoms.

* * * * *